(12) United States Patent
Konchitsky

(10) Patent No.: US 9,420,973 B1
(45) Date of Patent: *Aug. 23, 2016

(54) APPARATUS, DEVICE AND METHOD FOR VALIDATING ELECTROCARDIOGRAM

(71) Applicant: Alon Konchitsky, Santa Clara, CA (US)

(72) Inventor: Alon Konchitsky, Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/794,744

(22) Filed: Jul. 8, 2015

Related U.S. Application Data

(63) Continuation-in-part of application No. 13/854,461, filed on Apr. 1, 2013, now Pat. No. 9,107,597.

(51) Int. Cl.
| | |
|---|---|
| *A61B 5/044* | (2006.01) |
| *A61B 5/00* | (2006.01) |
| *A61B 5/0408* | (2006.01) |
| *A61B 5/0432* | (2006.01) |
| *A61B 5/04* | (2006.01) |

(52) U.S. Cl.
CPC .............. *A61B 5/684* (2013.01); *A61B 5/0006* (2013.01); *A61B 5/044* (2013.01); *A61B 5/0408* (2013.01); *A61B 5/04012* (2013.01); *A61B 5/0432* (2013.01); *A61B 5/7203* (2013.01); *A61B 5/7221* (2013.01); *A61B 5/7475* (2013.01)

(58) Field of Classification Search
CPC ............ A61B 5/04085; A61B 5/0408; A61B 5/0452; A61B 5/04028; A61B 5/684; A61B 5/0432; A61B 5/04012
USPC ........................................ 600/512, 513, 523
See application file for complete search history.

(56) References Cited

U.S. PATENT DOCUMENTS

| | | | |
|---|---|---|---|
| 9,107,597 B2 * | 8/2015 | Konchitsky | ........ A61B 5/04085 |
| 2014/0194760 A1 * | 7/2014 | Albert | ...................... A61B 5/70 600/509 |
| 2014/0228665 A1 * | 8/2014 | Albert | .................. A61B 5/6898 600/384 |

* cited by examiner

*Primary Examiner* — Edward Moran
*Assistant Examiner* — Michael Carey

(57) ABSTRACT

Embodiments of the present invention provides an apparatus containing a device communicably coupled to two electrodes that may be positioned on a body of a subject for obtaining 12 leads or 18 leads electrocardiogram. The two electrodes may obtain signal parameters such as arm leads (I, II, III, AVRAVL and AVF) and left chest leads (V1, V2, V3, V4, V5, V6) and right chest leads (V1R, V2R, V3R, V4R, V5R, V6R). The signal parameters may be detected and collected by the device for processing thereof and thus obtain 12 leads or 18 leads electrocardiogram that may be transmitted to a health care provider for seeking health assistance based on the transmitted electrocardiogram. Herein, the collected recorded signal parameters may further be processed to determine correctness thereof prior to transmitting the determined electrocardiogram to a monitoring station. Further, a method for obtaining the electrocardiogram using two electrodes is also provided.

21 Claims, 12 Drawing Sheets

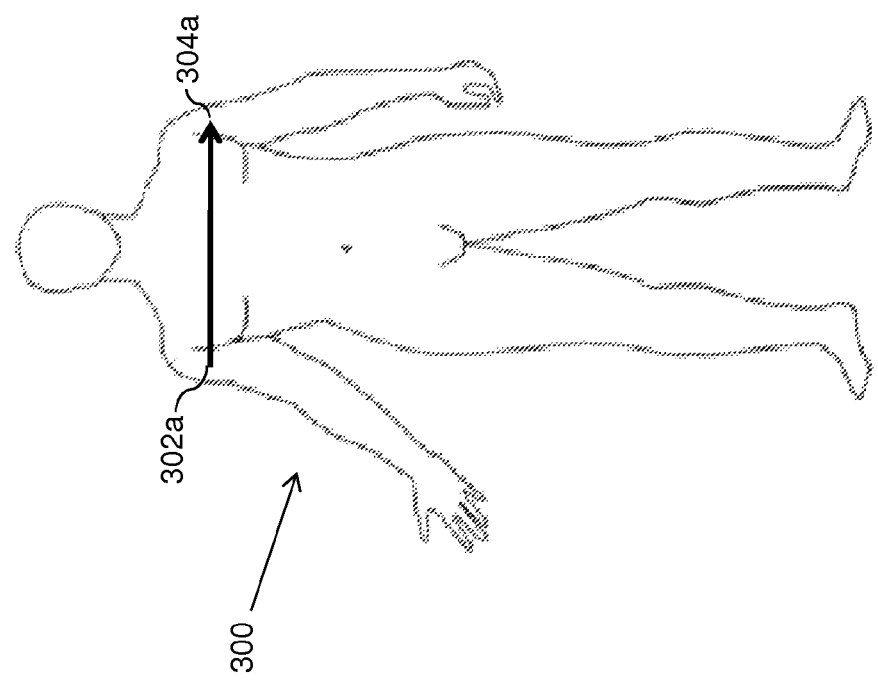

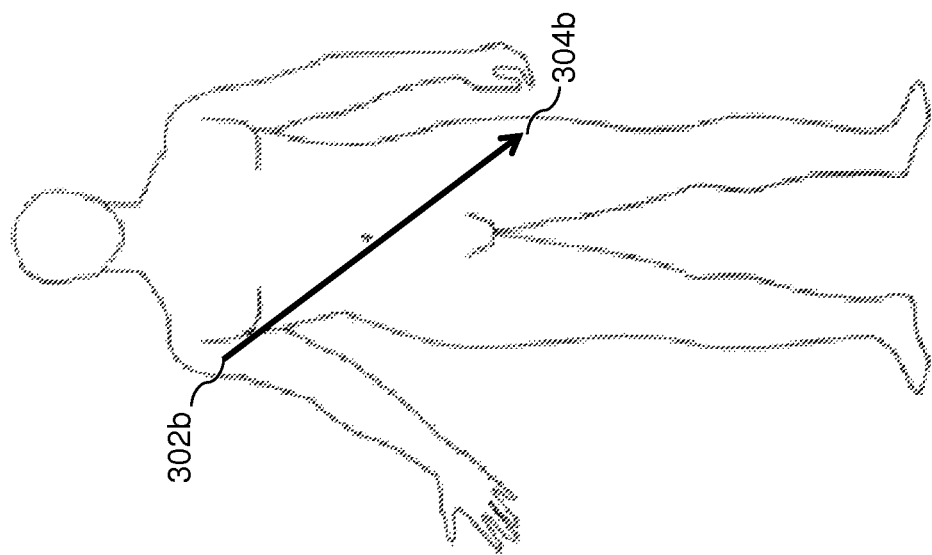

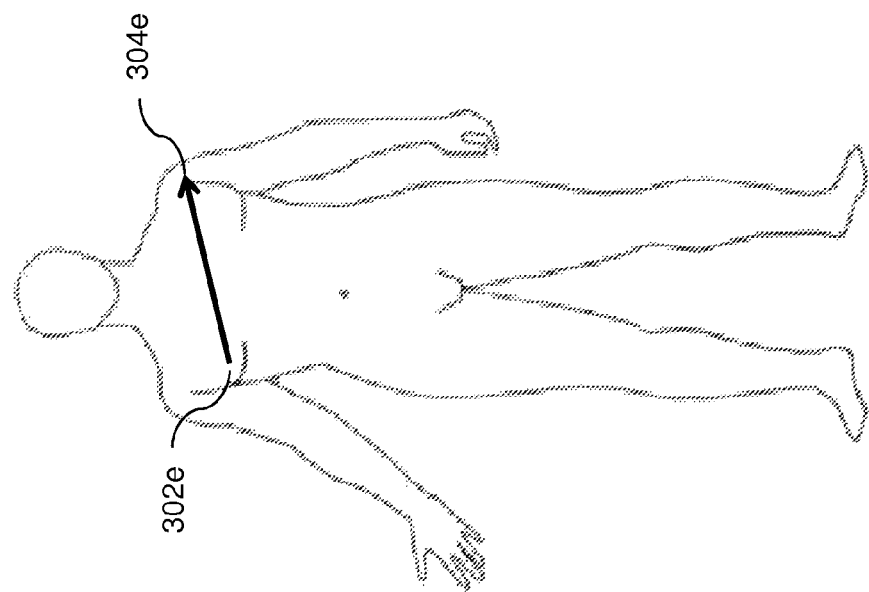

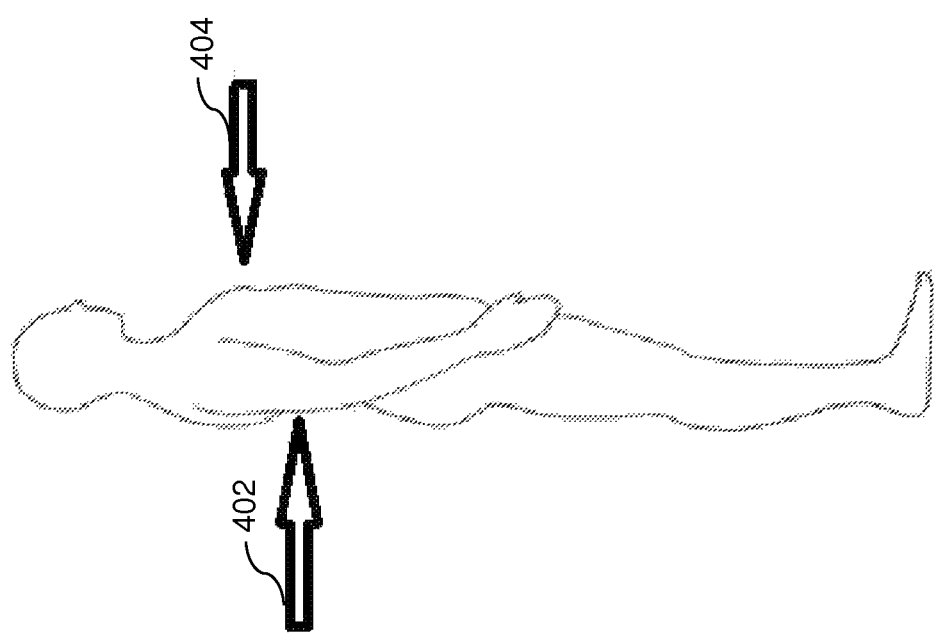

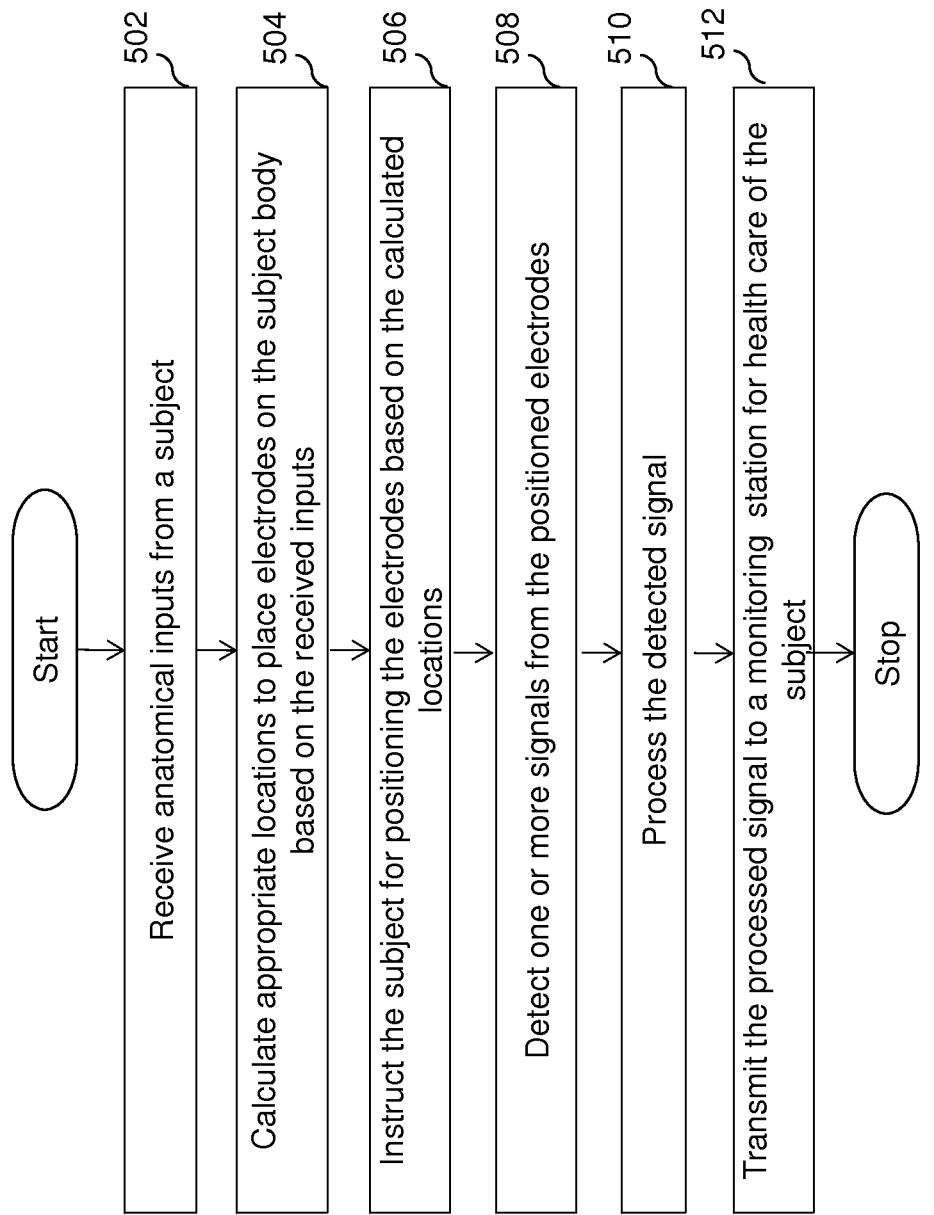

APPARATUS, DEVICE AND METHOD FOR VALIDATING ELECTROCARDIOGRAM

CROSS-REFERENCE TO RELATED APPLICATION

This application is a Continuation-in-part of U.S. patent application Ser. No. 13/854,461, (now U.S. Pat. No. 9,107, 597) filed Apr. 1, 2013.

TECHNICAL FIELD

Embodiments of the present invention relates to a device, system, and a method for medical diagnostic equipment. More particularly, embodiments of the present invention relates to a system and method for an electrocardiogram.

BACKGROUND OF THE INVENTION

In today's scenario, heart disease is a major type of abnormality found among people all over the world. The heart disease is a major source of mortality and mobility manifested in a wide range of symptoms. The most common symptom of the heart disease is chest pain. Chest pain can also be a common symptom in many diseases other than heart disease It can become incurable and more fatal, if proper medical assistance is not provided to a patient. An accurate and early diagnosis of the patient's condition can result in faster medical treatment and thus reduce morbidity and mortality.

Equipment used for detecting cardiac events is known as Electrocardiogram (ECG).ECG is mostly used for monitoring electrical activity of the heart. It is considered to be non-invasive and can provide immediate results.

Existing ECG machines are cumbersome and costly due to usage of number of electrodes that are attached to the body surface of the patient; namely, six positions for chest leads, and four positions for limb leads. Six limb-lead waveforms (I, II, III, AVR, AVL, and AVF) of standard 12-lead waveforms and six chest-lead waveforms (V1, V2, V3, V4, V5, and V6) of the same are derived from electric potentials of the heart that are detected and measured by the electrodes by measuring means. Diagnosis and treatment using several electrodes is possible in a hospital, or a clinic. However, accurate diagnosis of chest pain using ECG is not feasible when the patient is at remote location ((i.e., remote from any health center).

Some of the ECG units use remote devices such as, laptop, mobile phones, and telemedicine for diagnoses but do not provide accurate methods for diagnosing heart problems at a remote location (such as at home) that can be used in a simple way and do not require extensive medical knowledge before using the device.

For example US application number 2006224071 describes a method of recording 12 lead ECG with lesser number of electrodes. In this, the electrodes are located at V2 and V5 location points and at least one electrode at a level with V5 on right anterior auxiliary line, and at least one further electrode positioned on each of the right hand side and left hand side of the body. Although requiring a reduced number of electrodes in order to monitor 12 lead ECG, this method does require at least 5 electrodes including one in a very non-conventional location.

Similarly, PCT Publication WO 2004/038942 to LEE describes a 4 wired electrode recording using a mobile phone battery to detect an ECG rhythm (but not morphology). This application, however, does not indicate which locations are used and does not teach that a full 12 lead ECG may be inferred from the recordings. The electrodes are adhesive, fixed and must be placed in the correct position in order to achieve an accurate reading. In addition, the data is first transmitted to the telephone's battery and from there to the telephone itself. Finally, the method described in the above publications requires modifications in the telephone's hardware and software.

US Application Publication number 2006025695 describes a method for deriving a 12 lead ECG using a conversion matrix that allows the use of a smaller number of electrodes to predict a 12 lead ECG. However the described device uses 5 electrodes to obtain the 12 lead ECG recording. Furthermore, the application does not describe a wireless or mobile device that could analyze 12 lead ECG accurately.

European patent number EPI 188412 to Brodnick et al describes an ECG monitor connected to a plurality of lead wires, each lead wire having a transducer capable of receiving an ECG signal from a patient, the ECG monitor having a processor to process the ECG signals from the plurality of lead wires and produce ECG data representative of cardiac condition of the patient, with a wireless communication interface coupled to receive patient ECG data from the ECG monitor and to transmit patient ECG data to a health care provider. Again the issue of mobility is not addressed by Brodnick et al. in the patent application.

German patent number DE 10048746 describes a device for the receipt and conversion of ECG-signals with three electrodes which are applied to the upper torso of the patient and which are connected via a cable to an ATD converter; however the method does not produce a 12 lead ECG which is sufficiently accurate for diagnosis.

German patent number DEI 9707681 to Erbel et al. relates to a mobile telephone comprising housing, a transmitter, at least one receiver, a call number memory and buttons located on the housing. The device is configured in such a way that at least one emergency call button is mounted on the housing. However it does not teach or suggest obtaining a specific ECG configuration.

U.S. 60/820,780 (WO/2008/015667) by Cardicell LTD and Berkner, Lior describes a device utilizing three to four electrodes which is purported to record a 12-lead ECG. Most of the description relates to use of two subunits, each with two electrodes, for a total of four electrodes.

Based on the aforementioned, a device and a corresponding method are required for obtaining at least a 12 lead electrocardiogram (ECG) by utilizing a simple and cost effective mechanism that can be utilized by any user even at remote location without requiring direct assistance in measuring electrocardiogram from a health care provider. Further, the device should be operable with ease by utilizing a reduced number of electrodes.

SUMMARY

Embodiments in accordance with the present invention provide an apparatus for performing one of 12 leads and 18 leads electrocardiogram on a body of a subject. The apparatus comprises two electrodes. The two electrodes may be adjusted on the body of the subject to record one or more signal parameters at one or more locations on the subject's body. Further, the apparatus includes a device that is capable of being communicably coupled to the electrodes. The device is further configured to detect and collect the one or more recorded signal parameters for processing thereof and thereby determining one of 12 leads and 18 leads electrocardiogram, wherein the collected signal parameters being processed prior to transmitting the determined electrocardiogram to a monitoring station. Herein, the collected recorded signal parameters are further processed to determine correctness thereof prior to transmitting the determined electrocardiogram to a monitoring station.

Herein above, the collected recorded signal parameters are determined as incorrect when the recorded signals exceed a predefined (minimum or maximum) threshold level. The device is further configured to provide a notification (to a display) when the recorded signal parameters are determined as incorrect. The notification may include a probable reason for incorrect recorded signals. The device may further be capable of providing one or more suggestions when the recorded signal parameters are determined as incorrect. The suggestions may correspond to the probable reason for incorrect recorded signals.

Embodiments in accordance with the present invention further provide a device for performing one of 12 leads and 18 leads electrocardiogram. The device comprises a communication module for receiving one or more inputs from a subject. The device further comprises a measuring module for identifying appropriate locations for placing one or more electrodes on a body of a subject based on the received input, wherein the appropriate locations of the electrodes enable recording of one or more signal parameters by the electrodes. In addition, the device comprises a sensor module for detecting the recorded signal parameters and a processor module configured for analyzing and enhancing the signals parameters for determining one of 12 leads and 18 leads electrocardiogram, wherein the communication module transmits the determined electrocardiogram to a monitoring station. Herein, the processor is further configured to analyse the recorded signal parameters to determine correctness thereof prior to transmitting the determined electrocardiogram to the monitoring station.

Embodiments in accordance with the present invention further provide a method for performing one of 12 leads and 18 leads electrocardiogram on a body of a subject. The method includes steps of receiving one or more inputs from the subject, determining appropriate locations for positioning one or more electrodes on the body based on the received inputs, wherein the electrodes record one or more signal parameters from the body of the subject when the electrodes positioned on the appropriate locations, detecting the one or more signal parameters from the positioned electrodes, and processing the detected signal parameters for enhancement thereof to determine one of 12 leads and 18 leads electrocardiogram. Herein, the recorded signal parameters are analysed to determine correctness thereof, prior to transmitting the determined electrocardiogram to the monitoring station.

Further, in an embodiment, an apparatus of the present invention may include a dynamic reference electrode may be used is used for recording an electrocardiogram (ECG) such that each electrical difference between the two electrodes is calculated in relation to one other (reference) electrode(s) sequentially or simultaneously (although preferably simultaneously or at least in parallel). Herein, the reference electrode (s) is an electrode that may not be involved in direct measurement of electrical dipole. For each lead calculation the reference electrode is different (hence 'dynamic'), so in a system comprising only 2 electrodes, the reference electrode may be different and may shift for each lead measurement. This may be done by a designated software and/or hardware optionally comprising a switch. Further, the dynamic reference electrode may be utilized preferably done in order to calculate the limb leads between two electrodes is calculated in relation to said reference electrode, sequentially or simultaneously.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted the terms "comprising", "including", and "having" can be used interchangeably.

The preceding is a simplified summary of the present invention to provide an understanding of some aspects of the present invention. This summary is neither an extensive nor exhaustive overview of the present invention and its various embodiments. It is intended neither to identify key or critical elements of the present invention nor to delineate the scope of the present invention but to present selected concepts of the present invention in a simplified form as an introduction to the more detailed description presented below. As will be appreciated, other embodiments of the present invention are possible utilizing, alone or in combination, one or more of the features set forth above or described in detail below.

BRIEF DESCRIPTION OF THE DRAWINGS

Having thus described the invention in general terms, reference will now be made to the accompanying drawings, which are not necessarily drawn to scale, and wherein

Figure 1:
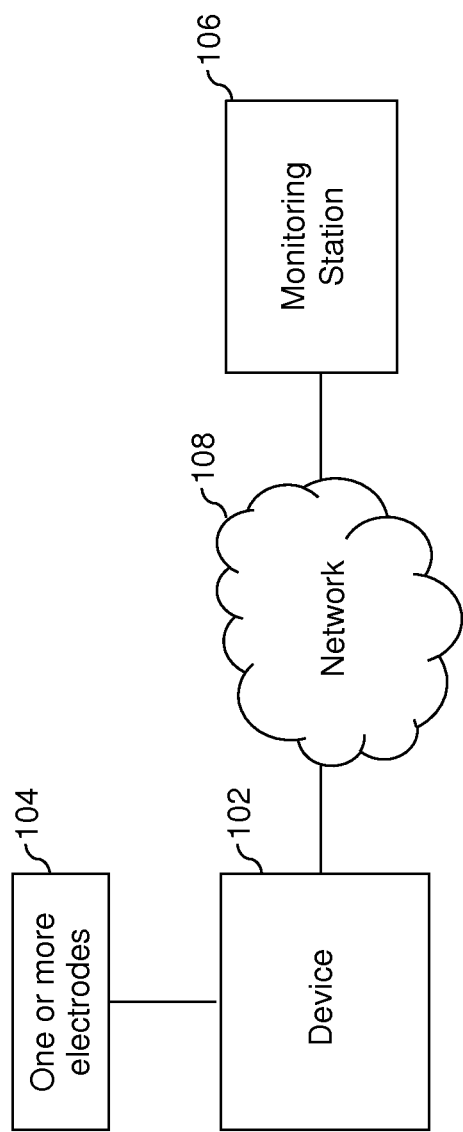
Figure 2:
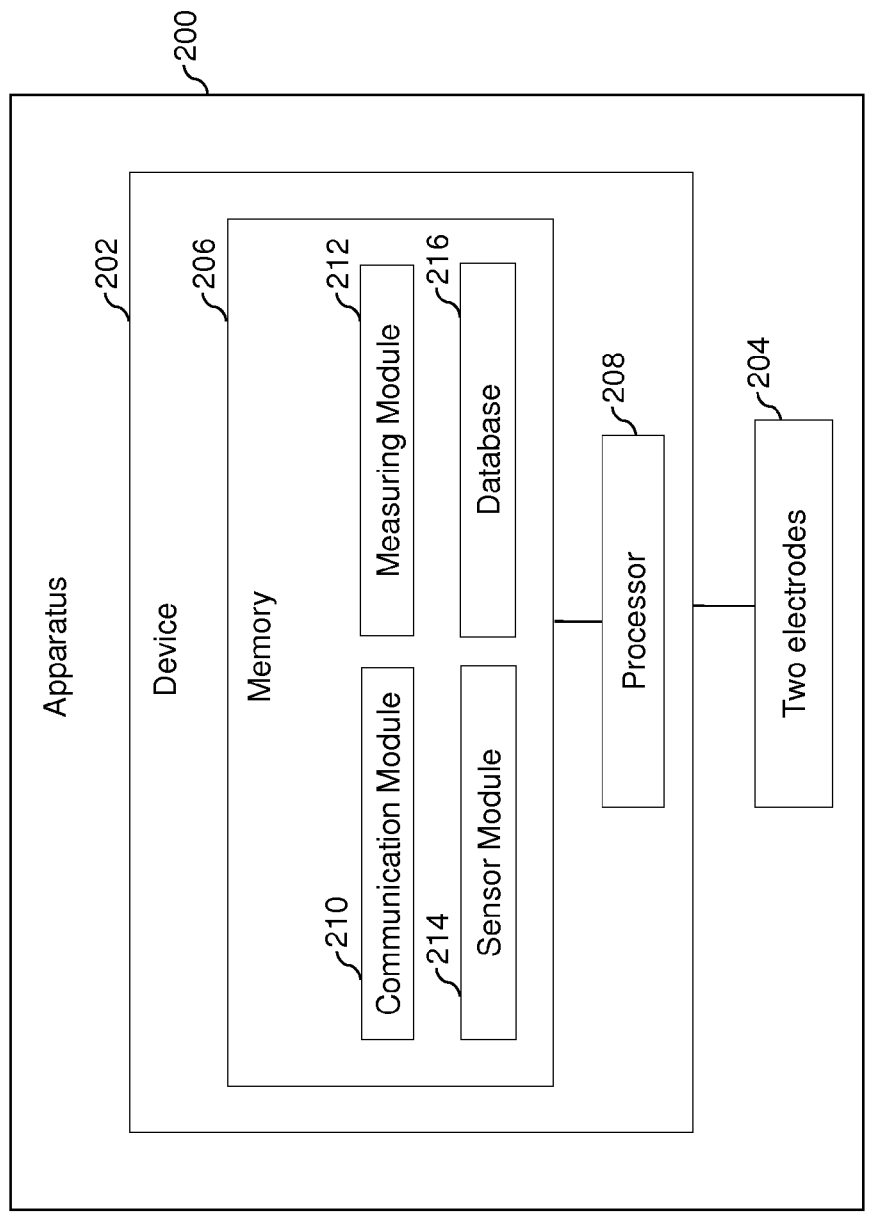
Figure 4B:
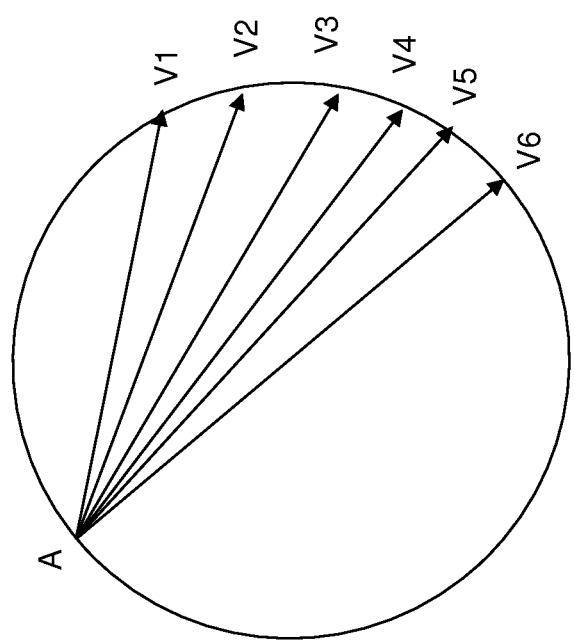
Figure 4C:
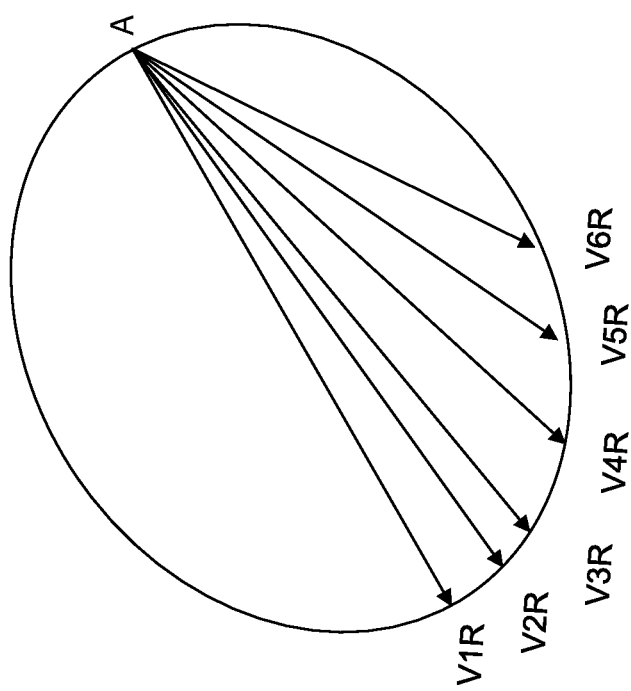

FIG. 1 illustrates an exemplary environment where various embodiments of the present invention are implemented;

FIG. 2 illustrates a block diagram of an apparatus for performing 12 leads or 18 leads electrocardiogram, in accordance with an embodiment of the present invention;

FIGS. 3A-3F illustrate positioning of two electrodes to obtain one or more signal parameters and thereby for performing 12 leads or 18 leads electrocardiogram, in accordance with one embodiment of the present invention;

FIG. 4A illustrates positioning of electrodes for obtaining chest leads, in accordance with an embodiment of the present invention;

FIG. 4B illustrates vector directions when measuring chest leads in accordance with one embodiment of the present invention;

FIG. 4C illustrates vector directions when measuring chest leads in accordance with another embodiment of the present invention; and FIG. 5 illustrates an exemplary method flow diagram for obtaining electrocardiogram, in accordance with an embodiment of the present invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including but not limited to. To facilitate understanding, like reference numerals have been used, where possible, to designate like elements common to the figures.

DETAILED DESCRIPTION

In the following detailed description, numerous specific details are set forth in order to provide a thorough understanding of embodiments or other examples described herein. In some instances, well-known methods, procedures, components and circuits have not been described in detail, so as to not obscure the following description.

Further, the examples disclosed are for exemplary purposes only and other examples may be employed in lieu of, or in combination with, the examples disclosed. It should also be noted the examples presented herein should not be construed as limiting of the scope of embodiments of the present disclosure, as other equally effective examples are possible and likely.

The present invention provides an apparatus, device and a corresponding method for obtaining 12 leads or 18 leads electrocardiogram (ECG) from measurement obtained with two electrodes. The usage of two electrodes provides an easy solution to a user for self analysis of his/her cardiac condition without requiring direct assistance from a health care provider for recording of health conditions of the user.

The two electrodes may be placed on a surface of human body at a location that may be determined by a device communicably coupled to the electrodes. In an embodiment, the device may be any wearable device (such as a wrist band, a watch and the like) having a control unit to control electrodes for measuring the health condition of the user. In another embodiment of the present invention, the device may optionally be a mobile and more preferably able to provide results of accurate ECG to a remote location, for example, through wireless, wire line or fiber optic communication. The device may further communicate the health condition of the user to a monitoring station that may be located at a remote location from the location for obtaining a comprehensive electrocardiogram using the two electrodes. Accordingly, the monitoring station may contact the user for providing the required health assistance.

FIG. 1 illustrates an exemplary environment where various embodiments of the present invention are implemented. As depicted, a device 102 may be connected to one or more electrodes 104 for recording various cardiac conditions when the electrodes are placed on a surface of user body. In a preferred embodiment, the device 102 may be communicably coupled to only two electrodes for recording the cardiac conditions. The device 102 may determine information corresponding to appropriate location on the user body for placing the electrodes thereon. The determined information corresponding to the appropriate location may be provided to the user so that the user may place the electrodes at the appropriate location for recording of one or more signal parameters such as one or more leads of limb, left chest, and right chest.

In a preferable embodiment, two electrodes may be used for obtaining electrocardiogram. Specifically, the two electrodes may be placed on the different locations on the surface of the user's body to subsequently measure one or more signal parameters. The device 102 and the electrodes 104 may be communicably coupled through connecting means that may be wired or wireless. The wired means may include cables that may be utilized to connect the electrodes 104 to the device 102. Further, the wireless means may include Bluetooth, Wi-Fi and so on.

The device 102 may receive signal parameters from the electrodes 104 that may be processed further to obtain electrocardiogram for 12 leads or 18 leads depending on the recording of the signal parameters at a number of locations of the user's body The signal parameters may be processed by first analyzing and enhancing the signal parameters for obtaining electrocardiogram for each waveform.

The electrocardiogram may be recorded by the device 102 and transmitted to a monitoring station 106 through a network 108. The monitoring station 106 may include a health care center for providing health care solution to the user based on the electrocardiogram that may be transmitted (to the monitoring station 106) by the device 102. In an embodiment, the monitoring station 106 may include a dedicated receiver for receiving electrocardiogram from the device 102. For example, the monitoring station 106 may include at least one of a mobile phone, a laptop computer, a Smartphone, a PDA and a pager corresponding to a heath center for providing one or more health services to the user (subject) based on the transmitted electrocardiogram.

In an embodiment, the device 102 may transmit the processed signal (electrocardiogram) to a smart phone that may then be transmitted to the monitoring station 106. Further, in an embodiment, the device 102 may process the signal parameters by converting the analog signal to digital signal and the processed signal parameters may then be transmitted to the monitoring station 106 for further processing thereof. The transmitted signals may be one or more waveforms that may be analyzed by the monitoring station 106 for providing health assistance to the user.

FIG. 2 illustrates a block diagram of an apparatus 200 for performing 12 leads or 18 leads electrocardiogram, in accordance with an embodiment of the present invention. The apparatus 200 may include, but is not limited to, a device 202 (similar to the device 102), and two electrodes 204 (similar to the one or more electrodes 104). The device 202 may be wearable like a watch or a wrist band that may be worn by the user. The device 202 may be communicably coupled to the two electrodes 204.

In an embodiment, the two electrodes 204 may be attached to the device 202 via stretchable/concealable wires such that when the electrodes 204 are not being used then the electrodes 204 may be retracted and completely concealed within the body of the device 202. In another embodiment, one electrode is not stretchable but is physically attached to a part of the device 202 (such as a watch or the watch band) while the other electrode may be attached to the wire. The device 202 may include a memory 206 and a processor 208. The memory 206 may include one or more modules such as a communication module 210 and a measuring module 212, a sensor module 214 and a database 216. Each module may include one or more instructions that may be executed by the processor 208.

The communication module 210 may include instructions to communicate with the two electrodes 204 and with a subject (hereinafter may interchangeably be referred to as 'user'). The user may provide inputs to the device 202 that may be received by the communication module 210. The inputs may correspond to, but are not limited to, anatomical inputs of the user such as a distance between two fixed anatomical points on the upper torso, such as the nipples or clavicles, and/or the circumference of the upper torso. The user may measure such anatomical inputs and then preferably enter the measured inputs to the device 202.

Additionally, the user may optionally move the device 202 from a first fixed anatomical point to a second fixed anatomical point so that the measuring module 212 may perform an automatic measurement of the distance between the two points. After measurement is completed, the measuring module 212 may again use this data in order to calculate where the V1 to V6 locations are located.

Such anatomical inputs may be provided by the user for enabling the device 202 to determine appropriate locations for placing the two electrodes 204 on a surface of the user's body. Specifically, a measuring module 212 may determine the appropriate locations for placing the electrodes on the user's body for each signal parameter corresponding to the user's body. The appropriate locations (i.e., correct placement) of the two electrodes may be required to determine signal parameters such as lead I, Lead II, Lead III, AVR, AVL and AVF for particular portions of the user's body. Further, the signal parameters may include left sided chest leads and right sided chest lead.

Specifically, for lead I, one electrode may be placed on the upper right arm and the other on upper left arm; For lead II one lead may be placed on the upper right arm and the other on their lower body; For lead III one electrode may be placed on the upper left arm and the other on the lower torso; For AVR one electrode may be held at the left nipple and the other on the upper right arm; for AVL one electrode may be held at the right nipple and the other at the upper left arm; For AVF one electrode may be held at the cricoids notch and the other at the upper left leg or the lower torso.

Further, for the chest leads one electrode may be held to the back, as high as the patient is able to place the electrode. The second electrode may be placed sequentially at the traditional locations for V1 through V6. For right sided chest leads, the second electrode may sequentially be placed at the traditional locations for V1R through V6R. Based on the aforementioned, the measuring module 212 may use such inputs to further calculate where the locations corresponding to V1 to V6 may be located. Further, in an embodiment, the V1 to V6 may refer to signal parameters that may be the appropriate locations for recording on chest or upper torso.

Further, the measuring module 212 may identify the appropriate locations for placing the electrodes 204 to record the signal parameters through a graphic presentation. The graphical presentation such as an image of the user's body (where the electrodes need to be placed for acquiring the signal parameters) may be provided to the device 202. Further, in an embodiment, such graphical presentation may be provided to a monitoring station (not shown) for identification of the appropriate locations for placing the electrodes on the user's body.

In an embodiment, the graphical presentation of the user's body may be provided by obtaining an image of the user's body, for example optionally with a camera, through ultrasound, or alternatively with some other type of location signaling. In this manner the user may be able to know where the unit is currently located in relation to the next correct and appropriate location. For example, the user may place a first electrode on the body and such placement may be provided to the measuring module 212 through the graphical representation thereof.

Once the appropriate location of the electrode is reached, the measuring module 212 may preferably indicate this to the user, for example with a signal such as a light, sound or vibration, or combination thereof, and may indicate that a signal corresponding to the correct placement of the electrode has been acquired. Once the signal has been acquired, the device 202 may optionally instruct the user to continue on to the next location. Specifically, the communication module 210 may instruct the user either verbally or through user interface (common beeps for example) regarding achieving the correct placement of the first electrode. Similarly, the device 202 may provide assistance to the user for an appropriate placement of the next electrode.

Further, the inputs received by the communication module 210 (from the user) may include other inputs in addition to the anatomical inputs (for determining positions of the electrodes on the user body). The other types of inputs may be to provide an indication to the device as which signal parameter (lead) is to be recorded next. For example, before recording a particular lead, the user operating the device 202 may indicate by using one or more controls (such as by compressing one or more buttons (controls)) on the device, that which signal parameter (lead) may be recorded next. Thus, the subject may be enabled to activate or deactivate recording of the signal parameters through the electrodes.

Once the cardio-electric signals (hereinafter may interchangeably be referred to as 'signal parameters') are acquired and recorded by the electrodes from the determined appropriate locations, the sensor module 214 of the device 202 may detect such signal parameters and the communication module 210 may receive and collect the signal parameters from the electrodes 204. The collected signals may be processed by the processor 208 to conduct the 12 leads or 18 leads electrocardiogram. In an embodiment, the signal parameters may be transmitted to the communication module 210 during recording of the signal parameters by the electrodes 204.

In an embodiment, the recorded signals or the signal parameters may be analyzed by the processor 208 to determine correctness thereof. If the recorded signals depict an unusual reading that may be beyond a predefined minimum or maximum threshold level then the processor 208 may generate a notification message/signal to the subject (user). Such notification message may depict an error message along with a probable reasoning therefor. For example, the recorded signals or the signal parameters may be checked for accuracy and if the recorded signals depict minimal reading (with low signal strength) or unusual/impractical signal parameters (that may exceed the threshold level) then the device may determine the probable reasoning thereof and accordingly notify the subject (user) in case of inaccurate reading. Such inaccuracy in the reading (of the recorded signal) may be due to various factors such as (but not limited to) displacement of the electrode(s) from the appropriate position, improper functioning of any of the electrodes and so on. Further, in an embodiment, the notification may additionally be provided to communication module 210 (or to the monitoring station), if the transmitted signals (recorded signal or signal parameters) are determined as inaccurate due to any of the aforementioned factors (such as displacement of electrode(s) or improper working of the electrodes and so on).

Additionally, based on the determined reasoning of the inaccurate reading (of the recorded signal), the device may further suggest at least one corrective measure such as the required displacement in position of the electrode(s), replacement of the non-functioning electrodes and so on, for receiving accurate reading from the electrode. In an embodiment, such suggestions may be provided (to a display) based on the user's profile (user's information), user's medical history and other past record of the user. For example, once the user is recognized by the device based on the user's profile or through image detection of the user, the device may compare the past record with the current record to determine probable reasoning for the inaccurate recorded signals. For example, the device may compare previously stored readings of the recorded signals with the currently recorded signals. Further, the device may compare the previously used location for positioning the electrodes (on the user's body) with the currently used location for positioning the electrodes. The reasoning determined by the device may not be restricted to aforementioned description. Further, various other factors that may be pre-stored corresponding to the user may be analysed by the processor 208 while analysing the recorded signals (that may be received as input from the electrodes) to determine a probable reasoning for improper readings corresponding to the recorded signals. As described herein above, the probable reasoning may be utilized for determining an appropriate location for positioning the electrode. Further, the probable reasoning may be utilized to rectify any possible human error or device error. For example, the probable determined reasoning may depict improper functioning of the electrode that may be corrected accordingly for accurate signal recording.

Specifically, the processor 208 may analyze and enhance the recordings to obtain a known electrocardiograph based on health condition of the user. Further, in an embodiment, the apparatus 200 may have an additional component (or device) for determining electrocardiograph based on the detected signals. Such additional component may include any type of processor configuration that may include, but not limited to, a data processor with memory, a logic gate, firmware, hardware and the like, or any combination thereof.

In an embodiment, processing of the recorded signal parameters may optionally be undertaken by an external processor, for example, including but not limited to, a mobile or cellular telephone, a call center, PDA, laptop computer, desktop computer, or a server, or any other computer. Optionally and preferably the raw data may be communicated to the processor (such as the processor 208 or other external processor) through wireless communications, including, but not limited to, Bluetooth, cellular protocol, IrDA protocol, optical communication, Wi-Fi, WLAN and the like.

Alternatively or additionally, the recorded signals (or signal parameters) may be transmitted to a call center or back office or any monitoring station. According to some embodiments of the present invention, more accurate acquisition of the cardio-electric signals may optionally and preferably be performed with a software that is running on a device, such as the device 202 in the apparatus 200.

In case a contact between the device 202 and the electrodes 204 is lost or if the device 202 does not receive any information (such as signal parameters) from the electrodes then the device 202 may issue an alert (warning) to the subject corresponding to placement of the electrodes on the body of the user. For example, the device 202 may issue a warning that the localization of the next recording may be incorrect due to displacement of any of the two positioned electrodes. Further, a warning may optionally and preferably appear when the recording time is insufficient (so that the signal is not fully acquired) and/or when the signal quality is low. Such warnings may be communicated to the user through the communication module 210 of the device 202. In an embodiment, the warnings may be communicated verbally or by displaying an indication in the form of light or may display a warning message to the user on any display such as related to the user's mobile phone or specific display (not shown) corresponding to the device 202.

The device 202 may further record the signal parameters along with information corresponding to the user (hereinafter may interchangeably be referred to as 'user information') in the database 216 of the memory 206. The user information may include, but is not limited to, personal information of the user, health information of the user (i.e., related to health of the user). Further, the database 216 may store one or more information corresponding to coordinates of the identified appropriate locations for placing the electrodes 204, an image of the body of the subject and medical information of the subject. In an embodiment, such information related to the user (i.e., stored coordinates and image) may be utilized in future for determining the appropriate positioning of the electrodes based on detection of the image of the subject. For example, in future treatments of the user, the image of the user may be detected through one or more existing techniques. Such detected image may be compared with one or more images stored in the database to retrieve the information corresponding to appropriate coordinates of the electrodes when match between the detected image and a stored image is found. Thus, the current information corresponding to the user's health check may be utilized in future to determine appropriate coordinates of the electrodes for placement thereof on the user's body. Further, in an embodiment, the current reading corresponding to the user's health may be utilized in future by comparing with the future reading (that may be obtained by using the same coordinates for positioning of the electrodes) to determine change in the user' health status. Furthermore, the database 216 may store medical history, most preferably including information regarding the cardiac history and status of the user (including but not limited to catheterization results, prior ECG's, echo results, stress test results and the like). The data can optionally be stored as video (for example for an angiogram, echocardiogram etc), images (for example CT, MRI), audio information and so on. Comparing the current ECG recording to the previously obtained ECG that may be stored in the memory 206, may increase specificity and sensitivity of diagnosis of cardiac abnormalities.

Additionally the user's medical history may optionally and preferably be accessed in case of an emergency by medical personnel and may also be used for identifying the specific user. Optionally the memory 206 may also store the upper torso locations corresponding to recoding the signal parameters.

According to some embodiments of the present invention, there is provided a mechanism to correctly identify the subject on whom the ECG was measured, as well as (additionally or alternatively) to preserve the privacy of such a subject. Due to the sensitive and personal information that may be contained in the memory 206 of the device 202, a number of optional identification confirmation measures may optionally be used to ensure that the device 202 and data contained within it, is personally accessed by the subject (and/or is accessed by authorized personnel such as medical personnel) using one or more authentication and identification methods. Such methods may optionally include but are not limited to, username and password, biometric identification (including but not limited to fingerprint or retinal scan), RFID and the like. Optionally the device 202 of the present invention may utilize a hash function to encrypt the subject's sensitive data or used for the identification of the subject.

According to some embodiments of the present invention, there are provided methods to interpret the ECG data. For example, optionally the electro-cardiac data is analyzed by the processor 208 or device's internal computational platform. The results are then optionally and preferably translated into an audio (preferably at least partially verbal) and/or graphic presentation that may be manifested on a display unit (for example the device 202 may relay to the layperson whether there is a need for medical assistance and its urgency; and/or indicate to trained personnel the exact condition the user is suffering from). Optionally, in case of an emergency the device 202 may automatically contact the emergency services (for example, if the device 202 is connected to a cellular telephone, an emergency call may optionally be placed through the telephone and/or any other type of telephone number).

According to another optional embodiment, which may optionally be implemented alternatively or additionally to the above embodiment, the cardio-electric signals are preferably transmitted to a back office or call center service. Trained personnel and/or designated software located in the device 202 may preferably analyze and decipher the signals. Alternatively, the transmitted data may optionally contain the already processed ECG recording, such that the trained personnel and/or designated software may be utilized to analyze the information (and relay it to the user). The processed or preprocessed raw data is optionally and preferably communicated to back office or the call center through any suitable communication mechanism.

The results may optionally be transmitted back to the user through any suitable communication mechanism as described herein, optionally including but not limited to MMS, SMS, two way communication module, voice communication, mobile or landline telephone, email, facsimile, a printer, or the like. Alternatively, trained personnel may optionally contact the user and provide medical advice according to the results (as well as optionally contacting local emergency services if required). Alternatively, the user may preferably be able to contact the back office or call center in order to convey further information regarding the user's condition and/or receive the results for the signals previously sent by the device 202.

Optionally the medical information stored in the device 202 may also be sent to the back office or call center. A professional consultation may optionally be provided in real time based on medical information, real time ECG and user's communicated medical information regarding current and/or prior symptoms or illnesses. This enables implementation of an exemplary 'pay per call' model, such that the user pays for each such consultation separately (at the time of consultation). Optionally, in case of an emergency the user may be located utilizing an optional GPS component installed in the device 202 so that the user's exact location may be ascertained. Alternatively, the user's location may optionally be identified using an external locating component (such as the one existing in the cellular connected to the device). According to some embodiments, one or more other optional features may optionally be provided. Optionally, the device 202 may be accompanied with an adaptor that may enable communication between the device 202 and any sort of handheld devices (e.g. cellular phones, PDAs etc.). The adaptor may be specifically tailored to the model of the handheld device used. An adaptor may also optionally be provided with regard to a power source and so forth.

Further, the device 202 may not be limited to the modules and components as described here-above and as illustrated in the FIG. 2. Further, the device 202 may include many other components that may be utilized for performing one or more functionalities for the purpose of the present invention. For example, the device 202 may have additional components such as a noise reduction component, a signal amplification component, a power source, I/O module and a display.

The noise reduction component of the device 202 may be utilized to remove noise signals from the electrocardiogram signals that may be produced by the device 202 by processing of the signal parameters. Further, the signal amplification component may be utilized to convert analog signals to digital signal and further to amplify the signals. A power source may optionally be a battery that may optionally be used once or that may be rechargeable.

Further, the I/O module may be an input output module that may function similar to the communication module 210. The I/O module may optionally be implemented using a wired or I/O port for example including, but not limited to, a plurality of USB port, serial port, optical port, PCMCIA, Ethernet, Infra Red, cellular telephone jack or port, or the like. The communication module (or the I/O module) may, for example, include but is not limited to Bluetooth, Wi-Fi, IrDA, WLAN, modem, dual communication, or the like. In an embodiment, the I/O module or the communication module 210 of the present invention may be used to communicate, in real time, the recorded electrocardiogram (ECG) signal to an external display unit including but not limited to a PDA, computer screen, television screen, mobile phone display or monitor, or the like or a combination thereof.

Optionally the device 202 may include communication with one or more other accessories (external or internal), such as a Pulse Oximeter, echocardiogram transducer, thermometer, capnograph, blood pressure cuff, fetal heart rate transducer, camera, wire electrodes, peak flow measurement apparatus and the like. These accessories may, alternatively, be connected to the device 202 optionally through one of the I/O plugs or wirelessly. The additional accessories may improve the diagnostic ability of the device 202 and provide a well rounded depiction of the user's state of health, According to some optional embodiments, each electrode may optionally feature a sticky stuff so as to position the electrode on correct location on the user's body. For example, the electrodes may have a gel dispenser for dispensing a conductive gel, for example upon contact with the skin and/or upon application of pressure and/or by pressing a designated button releasing the gel.

It may be appreciated by a person skilled in the art that the device is not limited to the apparatus, method and the device, as described above, for obtaining the 12 leads or 18 leads electrocardiogram. The present invention may include a system having modules, features and functionality similar to the apparatus 200. Thus, the system may include a device, such as the device 202, coupled to the two electrodes, such as the electrodes 204, for obtaining 12 leads or 18 leads electrocardiogram.

Further, the present invention is not limited to the embodiments described in this disclosure. Further various other embodiments may be implemented in light of the present invention. For example, in an embodiment, an apparatus of the present invention may include a dynamic reference electrode that may be used for recording an electrocardiogram (ECG) such that each electrical difference between the two electrodes may be calculated in relation to one other (reference) electrode(s) consecutively. In an embodiment, the electrical difference may be calculated sequentially or simultaneously (although preferably simultaneously or at least in parallel). Herein, the reference electrode (s) may be an electrode that may not be involved in direct measurement of electrical dipole.

For each lead calculation the reference electrode is different (hence 'dynamic'), so in a system comprising only 2 electrodes, the reference electrode may be different and may shift for each lead measurement. This may be done by a designated software and/or hardware optionally comprising a switch. Further, the dynamic reference electrode may be utilized preferably in order to calculate the limb leads. Additionally, the usage of certain terms such as 'first', 'second' in the present invention are for explanation purposes only and thus may not be construed as limiting for the present invention.

Figure 3C:
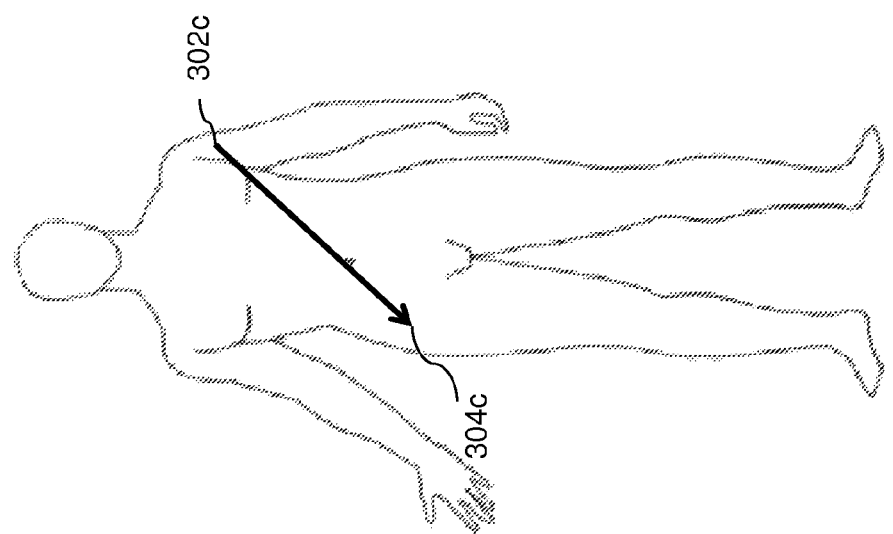

FIGS. 3A-F illustrate various positions of electrodes on a human body to record all cardio-electric signals that are required to generate a 12 lead or 18 lead electrocardiogram (ECG) for the human body. Specifically, FIGS. 3A to 3F depict placements of two electrodes for lead I, lead II, lead III, AVR, AVL and AVF respectively. As shown in FIG. 3A, two electrodes are placed on a subject 300. Subject may be any human being who may or may not have any knowledge of operating medical devices. Further, as shown, one of the two electrodes is placed at right arm of the subject (as shown with reference 302a) and another electrode is placed at left arm of the subject (as shown with reference 304a). This setup measures voltage between the right arm and left arm of the subject.

Further, the two electrodes may have different charge poles, such as if left arm of the subject 300 is connected with a positive pole (such as 302a) then flow of electric waves between the arms of the subject may be in a direction from reference point 302a to 304a, i.e., towards left arm of the subject 300. Such vector motion in the horizontal direction may cause an upward deflection of an ECG machine stylus on the paper. In this way an ECG graph can be obtained to determine direction and amount of electrical activity between arms of the subject. This setup is very useful in determining electrical activity moving in a horizontal direction.

As shown in FIG. 3B, two electrodes are placed on a subject 300. Further, as shown, one of the two electrodes is placed at right arm of the subject (as shown with reference 302b) and another electrode is placed at left leg of the subject (as shown with reference 304b). This setup measures voltage between the right arm and left leg of the subject. Further, it helps in measuring electric wave flow from the right arm to the left leg of the subject i.e., in a direction from reference point 302b to 304b of the subject 300. This setup is very useful in determining electrical activity moving in down and leftward direction of the body of the subject 300.

Further, as shown in FIG. 3C, two electrodes are placed on a subject 300. Further, as shown, one of the two electrodes is placed at left arm of the subject (as shown with reference 302c) and another electrode is placed at right leg of the subject (as shown with reference 304c). This setup measures voltage between the left arm and right leg of the subject. Further, it helps in measuring electric wave flow from the left arm to the right leg of the subject i.e., in a direction from reference point 302c to 304c of the subject 300. This setup is very useful in determining electrical activity moving in down and rightward direction of the body of the subject 300.

Figure 3D:
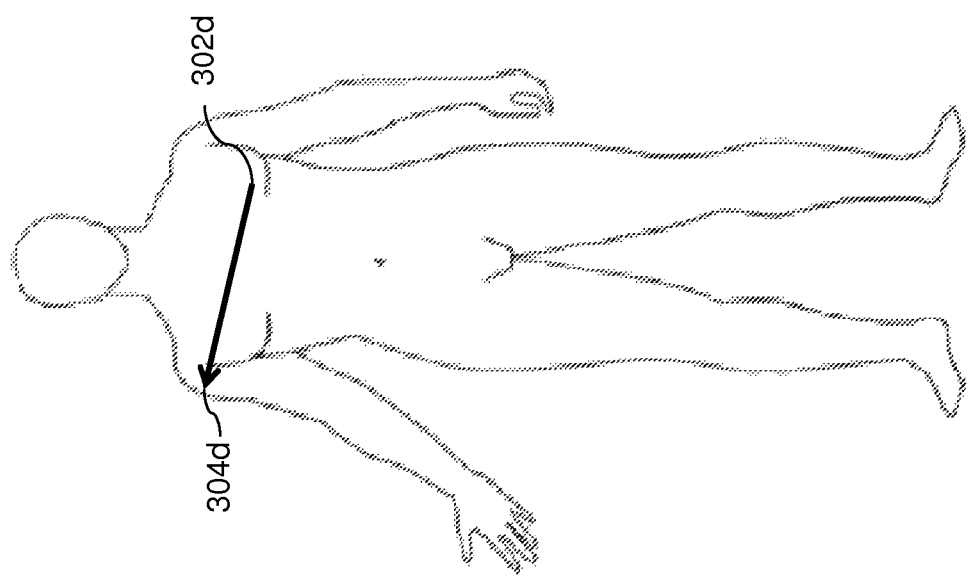

Furthermore, as shown in FIG. 3D, two electrodes are placed on a subject 300. Further, as shown, one of the two electrodes is placed at left side of subject's chest (as shown with reference 302d) and another electrode is placed at right arm of the subject (as shown with reference 304d). This setup measures voltage between the left chest area and right arm of the subject. Further, it helps in measuring electric wave flow from the left chest area to the right arm of the subject i.e., in a direction from reference point 302d to 304d of the subject 300. This setup is very useful in determining electrical activity moving in rightward and slightly upward direction of the body of the subject 300.

Further, as shown in FIG. 3E, two electrodes are placed on a subject 300. Further, as shown, one of the two electrodes is placed at right side of subject's chest (as shown with reference 302e) and another electrode is placed at left arm of the subject (as shown with reference 304e). This setup measures voltage between the right chest area and left arm of the subject. Further, it helps in measuring electric wave flow from the right chest area to the left arm of the subject i.e., in a direction from reference point 302e to 304e of the subject 300. This setup is very useful in determining electrical activity moving in leftward and slightly upward direction of the body of the subject 300.

Figure 3F:
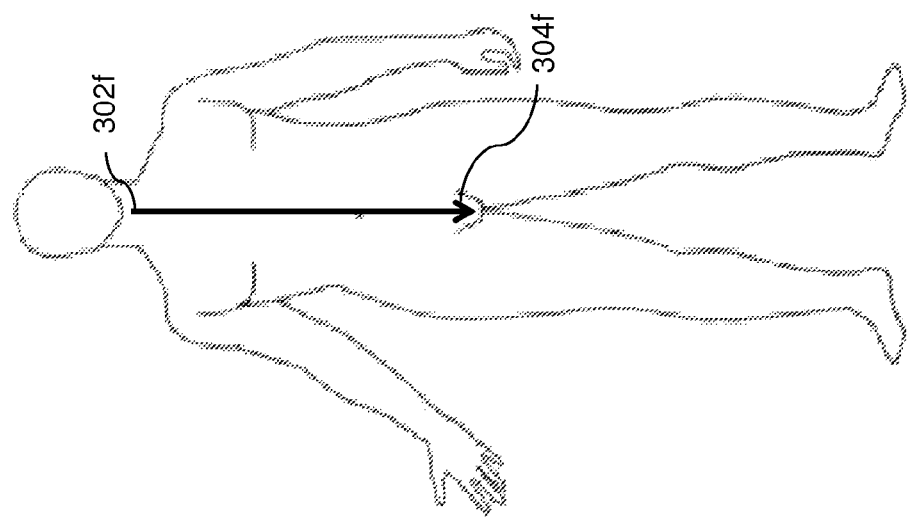

Furthermore, as shown in FIG. 3F, two electrodes are placed on a subject 300. Further, as shown, one of the two electrodes is placed in middle of subject's chest (as shown with reference 302f) and another electrode is placed at lower torso of the subject (as shown with reference 304f). This setup measures voltage between the chest area and lower torso of the subject. Further, it helps in measuring electric wave flow from the chest area to the lower torso of the subject i.e., in a direction from reference point 302f to 304f of the subject 300. This setup is very useful in determining electrical activity moving in vertical and specifically in downward direction of the body of the subject 300.

FIG. 4A illustrates positioning of electrodes for obtaining chest leads, in accordance with an embodiment of the present invention. According to some embodiments of the present invention, the cardio-electric signal may preferably be acquired in a consecutive manner utilizing the two electrodes in order to achieve a full 12 or 18-lead ECG. In general embodiment of the present invention, the same two electrodes may be used to record both the arm leads (I, II, III, AVR AVL and AVF) and the left chest leads (V1, V2, V3, V4, V5, V6) and right chest leads (V1R, V2R, V3R, V4R, V5R, V6R).

For the chest leads a first electrode is held to the back, as high as the subject (such as a patient) is able to place the electrode. The second electrode may be placed sequentially at the traditional locations for V1 through V6. For right sided chest leads the second electrode is sequentially place at the traditional locations for V1R through V6R.

As depicted through an arrow 402, the first electrode may be placed at the back of the subject. Similarly, the second electrode may be placed at the chest portion, as depicted by an arrow 404. The left sided chest leads may be acquired if the second electrode is placed on the left side of the chest at the traditional locations. The left sided chest leads may be depicted through V1, V2, V3, V4, V5 and V6. Similarly, the right sided chest leads may be acquired if the second electrode is placed on the chest at the traditional locations corresponding to the right sided chest leads. The right sided chest leads may be referred through V1R, V2R, V3R, V4R, V5R and V6R.

Further, the left sided chest leads and the right sided chest leads are depicted in FIGS. 4B and 4C. As shown, FIGS. 4B and 4C illustrate vector directions when measuring chest leads in accordance with different embodiments of the present invention. Specifically, as shown, the FIG. 4B depicts vector directions corresponding to the left sided chest leads V1 to V6 that may be acquired when one of the electrodes is set on the back of the subject (as depicted by a point 'A') while other electrode is set on the chest at the traditional locations corresponding to the left sided chest leads.

This setup measures voltage between the positions of the electrodes i.e., the voltage may be measured between the back of the subject and the chest positions of the electrode. Further, this helps in measuring electric wave flow from the back point (A') to the chest positions of the electrodes that are V1, V2, V3, V4, V5 and V6. This set up may be useful in determining electrical activity on the left sided chest of the subject.

Similarly, as shown, the FIG. 4C depicts vector directions corresponding to the right sided chest leads V1R, V2R . . . to V6R that may be acquired when one of the electrodes is set on the back of the subject (as depicted by a point 'A') while other electrode is set on the chest at the traditional locations corresponding to the right sided chest leads.

This setup of electrodes enables measurement of voltage between the positions of the electrodes i.e., the voltage may be measured between the back of the subject and the right sided chest positions of the electrode. Further, this helps in measuring electric wave flow from the back point ('A') to the chest positions of the electrodes that are V1R, V2R, V3R, V4R, V5R and V6R. This set up may be useful in determining electrical activity on the right sided chest of the subject. The concept of chest leads and corresponding positioning of electrodes for recording of the signal parameters is explained previously in this disclosure thus not repeated herein again for the sake of brevity.

FIG. 5 illustrates an exemplary flowchart depicting a method for enabling a layperson (hereinafter referred to as "subject") to obtain his/her electrocardiogram (ECG) by using a medical device (such as the device 202) with only two electrodes, in accordance with an embodiment of the present invention. The order in which the method is performed is not intended to be construed as limitation, and further any number of the method steps may be combined in order to implement the method or an alternative method without departing from the scope of the invention.

A subject may be any user who uses the medical device and may not necessarily have knowledge of operating the medical device. In an embodiment, the medical device with two electrodes may be configured to obtain a 12 lead or 18 lead electrocardiogram (ECG) by using the only two available electrodes.

In an embodiment, the medical device may have a housing for storing the two electrodes. Further, any of the two electrodes of the medical device may be referred to as a dynamic reference electrode for recording of at least one of one or more signal parameters. For example, location placement of second electrode may be in reference to location of first electrode. Further, the electrodes may have one or more connectivity means for enabling communicable coupling between the electrodes.

Further, the medical device may include a noise reduction component, a signal amplification component, a memory, and a display. Furthermore, the medical device may include a database for storing one or more information corresponding to the subject, the information comprises at least one of: coordinates of the identified appropriate locations for the electrodes, an image of the body of the subject and medical information of the subject. Further, the medical device may be configured to be a portable device that can be carried easily to remote locations for monitoring heart condition of the subject. Heart condition may include one or more of ischemic heart disease, acute myocardial infarction, arrhythmias, conduction defects, metabolic disease with heart related effect, or the like. In an embodiment, the electrodes of the medical device may be attached via stretchable/concealable wires such that when the electrodes are not being used they can be retracted and completely concealed within the body of the medical device.

Furthermore, the medical device may further include a transmitter. The transmitter may be used by the medical device to transmit data from the medical device to a remote station. In an embodiment, the transmitter may also be configured to transfer the data from the medical device to a nearby Smartphone, wherein the Smartphone may further be used to forward the data to the remote station. Further, the transmitter may use any wireless communications as known in the art, including but not limited to, Bluetooth, cellular protocol, IrDA protocol, optical communication, Wi-Fi, WLAN and the like.

In an exemplary embodiment of the present invention, the medical device with two electrodes is configured to acquire cardio-electric signals from heart of the subject in a consecutive manner by utilizing the two electrodes in order to achieve a full 12 or 18-lead ECG. The two electrodes may be used to record both arm leads of the subject (I, II, III, AVR AVL and AVF), left chest leads of the subject (V1, V2, V3, V4, V5, V6), and right chest leads of the subject (V1R, V2R, V3R, V4R, V5R, V6R).

At step 502, the medical device with the two electrodes may receive anatomical inputs from the subject related to physical structure of the subject. The anatomical inputs may enable the medical device to calculate appropriate locations on the subject's body for using/placing the electrodes. In an embodiment, the anatomical inputs may include, but are not restricted to, torso dimensions. The torso dimensions may include distance between two fixed anatomical points on upper torso, such as the nipples or clavicles, and/or may measure the circumference of the upper torso.

At step 504, based on the anatomical inputs provided by the subject, the medical device may calculate appropriate locations on the subject's body for placing the electrodes. In an embodiment, the medical device may use a pre-defined algorithm to determine appropriate locations on the subject's body based on the received anatomical inputs from the subject. In an embodiment, based on the anatomical inputs received from the subject, the medical device may determine an appropriate distance that may be required between two electrodes while measuring cardio-electric signals. This distance may vary person to person based on body structure of the person. Further, the medical device may also be configured to store the anatomical inputs received from the subject to ensure that the subject needs not to provide same inputs each time while using the medical device. In an embodiment, the method may determine appropriate positions of the electrodes based on information corresponding to the subject. For example, the method may detect image of the subject and accordingly may retrieve the information (i.e., user information) from the database (as described previously in conjunction with FIG. 2) based on the detected image. Such information may include, but is not limited to, personal information including (but not restricted to) image of the subject, health information and information corresponding to previous health checkup (related to 12 leads or 18 leads electrocardiogram) performed on the body of the subject. Hereinafter, the information corresponding to the previous health checkup may interchangeably be referred to as 'medical information'. Herein, the previous medical information may include, but not limited to, coordinates corresponding to positioning of the electrodes, medical history and so on corresponding to previous health checkup(s) (performed in past) of the subject. Thus, once the subject is recognized (through image detection or through any other detection method), the method may automatically determine suitable coordinates for placement of the electrodes based on the previously stored medical information. Further, in this embodiment, the method may highlight the suitable coordinates on the subject's body. Further in an embodiment, the subject may be wearing a device (such as the device 202) that may include a lightening arrangement to highlight such suitable coordinates for positioning of the electrodes. It may be appreciated by a person skilled in the art that the method is not restricted to aforementioned embodiment(s) in determining and highlighting the determined coordinates for positioning of the electrodes. Further, various embodiments may be implemented for determining and thereby highlighting the determined coordinates on the subject's body.

At step 506, after determining the appropriate locations on the subject's body, the medical device may instruct the subject for positioning the electrodes on the determined locations of his/her body for measuring/recording one or more signal parameters. In an embodiment, the one or more signal parameters (such as arm leads and chest leads, as described previously in conjunction with FIG. 2) are acquired by the two electrodes in a consecutive manner. In addition, the medical device may provide certain controls to the subject for enabling the subject to perform one of activating and deactivating recording of the signal parameters through the electrodes.

Further, in an embodiment, the subject may hold the electrodes, one electrode with each hand, for positioning the electrodes at the appropriate position. In another embodiment, the electrodes may be sticky in characteristics for attaching the electrodes to the user's body. The medical device may provide a visual to the subject to illustrate an appropriate position to place the two electrodes. Further, a human body may have a plurality of appropriate locations for measuring/recording the signal parameters. Various embodiments may be used to position the electrodes on the body of the subject to measure/record signal parameters from all appropriate locations of the subject.

In first embodiment, one electrode is placed on the upper right arm and the other on upper left arm. In second embodiment, one lead is on the upper right arm and the other on subject's lower body. In third embodiment, one electrode is placed on the upper left arm and the other on the lower torso. In fourth embodiment, one electrode is held at the left nipple and the other on the upper right arm.

In fifth embodiment, one electrode is held at the right nipple and the other at the upper left arm. In sixth embodiment, one electrode is held at the cricoids notch and the other at the upper left leg or the lower torso. Further, in seventh embodiment, one electrode may be placed at the back of the subject while the other electrode may be on the left side of the chest. In eighth embodiment, one elected may be placed at the back of the subject while the other electrode may be placed on the right sided chest.

In an embodiment, all of the aforementioned embodiments may be performed consecutively to obtain a 12 lead or 18 lead electrocardiogram (ECG) by using only two available electrodes, wherein the electrodes may be required to be re-placed on multiple and different locations of the body for recording all cardio-electric signals that are required to form the 12 lead or 18 lead electrocardiogram.

At step 508, after positioning the two electrodes on a determined and appropriate position of the subject's body, the medical device may start detecting/receiving/recording one or more cardio-electric signals from the positioned electrodes. In an embodiment, if the medical device does not receive the signals, then the medical device may determine that the subject has not positioned an electrode on accurate position. The medical device may then inform the subject via suitable means such as by audio message or by audio message to instruct the subject to replace an electrode to a correct position. In an embodiment, the medical device may click/record a picture of the subject's body and may show the correct position to place the electrode by showing a mark on digital picture of the subject.

Further, in an embodiment, if during measurements of the signals at step 508, if contact of the electrode is lost with the body or if the electrode is moved away from the appropriate place, then the medical device may provide a warning to the subject to correct the placement of the electrode and while processing the recorded data, the medical device may add a meta data to label inconsistencies in the recorded data. In another embodiment, such warning may also be applied when the medical device determines that the recording time was not sufficient or the recorded signal was of low quality.

At step 510, based on the measured/recorded signals and signal parameters from accurate positions of the subject's body, the medical device may process the measured/recorded signal parameters by analyzing and enhancing them to create at least one of 12 leads and 18 leads electrocardiogram (ECG). In an embodiment, the signal parameters may be converted the analog signal to digital. Further, the recorded signals (or signal parameters) may be amplified and enhance the quality of the signal.

In an embodiment, collected recorded signal parameters are further processed to determine correctness thereof prior to transmitting the determined electrocardiogram to a monitoring station. Herein, the collected recorded signal parameters are determined as incorrect when the recorded signals exceed a predefined (minimum or maximum) threshold level. The device is further configured to provide a notification (to a display) when the recorded signal parameters are determined as incorrect. The notification may include a probable reason for incorrect recorded signals. The device may further be capable of providing one or more suggestions when the recorded signal parameters are determined as incorrect. The suggestions may correspond to the probable reason for incorrect recorded signals.

At step 512, after processing of the measured/recorded signals, the medical device may transmit (through wireless, wire line or fiber optic communication) the processed signals to a monitoring station for providing health care to the subject. In an embodiment, the monitoring station may include at least one of a mobile phone, a laptop computer, a Smartphone, a PDA and a pager corresponding to a heath center for providing one or more health services to the subject based on the transmitted electrocardiogram.

In another embodiment, the monitoring station may be a health center that has medical professionals trained to analyze electrocardiograms. Such medical professionals may analyze the received electrocardiogram of the subject and may determine whether or not the subject is required to take some action. The action may include certain medical procedures such as taking medicine or reporting to a medical professional etc. This may enable the subject to monitor and cure his/her heart's condition from any remote location.

Advantageously, the present invention may propose and provide an apparatus, system, and a method for obtaining a comprehensive 12 or 18-lead electrocardiogram (ECG) of a subject via only two electrodes (having two electrodes) instead of three or four electrodes. This eases a human being to use the proposed apparatus to perform "self recording" of ischemic events by holding one electrode in each hand in order to place the electrodes on appropriate body locations.

Further, the present invention guides the subject is determining and locating appropriate locations for placing the electrodes according to body structure of the subject. Furthermore, the present invention provides visual guidance to the subject for accurately positioning the electrodes. Moreover, the present invention proposes a method of alarming the subject in case if the cardio-electric signals being received by the electrodes are of low strength or if an electrode moves away from appropriate location of the body during recording of signals.

Furthermore, the apparatus proposed by the present invention is configured to be portable enough to ease the subject to carry the apparatus to any remote place. In an embodiment, the apparatus may be as portable as a wrist watch or can be worn as a wrist band. Further, the electrodes of the apparatus may be attached via stretchable/concealable wires such that when the electrodes are not being used they are retracted and completely concealed within the body of the watch apparatus. Furthermore, the proposed apparatus includes a transmitter for transmitting recorded electrocardiograms to medical professionals. The medical professionals may therefore be able to diagnose heart condition of the subject and may suggest remedies from a remote location.

It may be appreciated by a person skilled in the art that the present invention is not limited to the description provided above with the help of drawings. Further, positions, designs and sizes of various components, as shown in drawings, may not be considered as limiting. Various other embodiments in light of the scope of the present invention may be implemented.

While the foregoing is directed to embodiments of the present invention, other and further embodiments of the present invention may be devised without departing from the basic scope thereof. In particular, it should be appreciated that any element of any embodiments disclosed herein may be combined with any other elements from any other embodiments disclosed herein, in accordance with yet further embodiments of the present invention.

The present invention, in various embodiments, configurations, and aspects, includes components, methods, processes, systems, kits and apparatus substantially as depicted and described herein, including various embodiments, subcombinations, and subsets thereof. Those of skill in the art will understand how to make and use the present invention after understanding the present disclosure. The present invention, in various embodiments, configurations, and aspects, includes providing apparatus and processes in the absence of items not depicted and/or described herein or in various embodiments, configurations, or aspects hereof, including in the absence of such items as may have been used in previous devices or processes, e.g., for improving performance, achieving ease and reducing cost of implementation.

The foregoing discussion of the present invention has been presented for purposes of illustration and description. The foregoing is not intended to limit the present invention to the form or forms disclosed herein. In the foregoing Detailed Description for example, various features of the present invention are grouped together in one or more embodiments, configurations, or aspects for the purpose of streamlining the disclosure. The features of the embodiments, configurations, or aspects of the present invention may be combined in alternate embodiments, configurations, or aspects other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment, configuration, or aspect. Thus, the following claims are hereby incorporated into this detailed description, with each claim standing on its own as a separate preferred embodiment of the present invention.

Moreover, though the description of the present invention has included description of one or more embodiments, configurations, or aspects and certain variations and modifications, other variations, combinations, and modifications are within the scope of the present invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An apparatus for performing one of 12 leads and 18 leads electrocardiogram on a body of a subject, the apparatus comprising:
   two electrodes, each of the two electrodes being adjustable on the body to record one or more signal parameters at one or more locations on the body, the one or more electrodes comprise a dynamic reference electrode, the dynamic reference electrode not involved in direct measurement of an electrical dipole, the dynamic reference electrode shifting for each lead measurement; and
   a device capable of being communicably coupled to the electrodes, the device configured to detect and collect the one or more recorded signal parameters for processing thereof and thereby determining one of 12 leads and 18 leads electrocardiogram, wherein the collected recorded signal parameters are further processed to determine correctness thereof prior to transmitting the determined electrocardiogram to a monitoring station, and
   wherein the device is further configured to provide a notification when the recorded signal parameters are determined as incorrect, the notification including a probable reason for incorrect recorded signals.

2. The apparatus of claim 1, wherein the device further comprising a measuring module for identifying appropriate locations for placing the one or more electrodes on a body of a subject based on an input received therefrom, wherein the appropriate locations of the electrodes enable recording of the one or more signal parameters by the electrodes.

3. The apparatus of claim 2, wherein the measuring module identifies the appropriate locations for placing the one or more electrodes further based on pre-stored information corresponding to the subject.

4. The apparatus of claim 1, wherein the collected recorded signal parameters are determined as incorrect when the recorded signals exceed a predefined threshold level.

5. The apparatus of claim 1, wherein the device is further capable of providing one or more suggestions when the recorded signal parameters are determined as incorrect, the suggestions corresponding to the probable reason for incorrect recorded signals.

6. The apparatus of claim 1, wherein the device enables the subject to perform one of: activation or deactivation of recording of the signal parameters through the electrodes.

7. A device for performing one of 12 leads and 18 leads electrocardiogram, the device comprising:
   a communication module for receiving one or more inputs from a subject;
   a measuring module for identifying and displaying appropriate locations for placing one or more electrodes on a body of a subject based on the received input, the one or more electrodes comprising a dynamic reference electrode, the dynamic reference electrode not involved in direct measurement of an electrical dipole, the dynamic reference electrode shifting for each lead measurement; and a processor configured for analyzing and enhancing the signals parameters for determining one of 12 leads and 18 leads electrocardiogram, wherein the communication module transmits the determined electrocardiogram to a monitoring station and transmits, from information received from the measurement module, the next location to place an electrode, and wherein the processor is further configured to analyse the recorded signal parameters to determine correctness thereof prior to transmitting the determined electrocardiogram to the monitoring station.

8. The device of claim 7 further comprising a sensor module for detecting the recorded signal parameters.

9. The device of claim 7 further comprising a noise reduction component, a signal amplification component, a memory and a display.

10. The device of claim 7, wherein the appropriate locations of the electrodes enable recording of one or more of the signal parameters by the electrodes.

11. The device of claim 7 further comprising a database for storing one or more information corresponding to the subject, the information comprises at least one of: coordinates of the identified appropriate locations for the electrodes, an image of the body of the subject and medical information of the subject.

12. The device of claim 11, wherein the measuring module identifies the appropriate locations for placing the one or more electrodes further based on pre-stored information corresponding to the subject.

13. The device of claim 7, wherein the collected recorded signal parameters are determined as incorrect when the recorded signal parameters exceed a predefined threshold level.

14. The device of claim 13, wherein the communication module is further configured to provide a notification when the recorded signal parameters are determined as incorrect, the notification including a probable reason for incorrect recorded signals.

15. The device of claim 7, wherein the communication module is further capable of providing one or more suggestions when the recorded signals are determined as incorrect, the suggestions corresponding to the probable reason for incorrect recorded signals.

16. The device of claim 7, wherein the communication module is further configured to provide an alert to the subject corresponding to placement of the electrodes at the appropriate locations.

17. A method for performing one of 12 leads and 18 leads electrocardiogram on a body of a subject, the method comprising:

receiving one or more inputs from the subject;

using a measurement module for determining appropriate locations for positioning one or more electrodes on the body based on the received inputs, wherein the electrodes record one or more signal parameters from the body of the subject when the electrodes are positioned on the appropriate locations, the one or more electrodes comprising a dynamic reference electrode shifting for each lead measurement;

detecting the one or more signal parameters from the positioned electrodes; and processing the detected signal parameters for enhancement thereof to determine one of 12 leads and 18 leads electrocardiogram, wherein, the recorded signal parameters are analyzed to determine correctness thereof, prior to transmitting the determined electrocardiogram to the monitoring station.

18. The method of claim 17 further comprising transmitting to a display the appropriate locations for positioning one or more of the electrodes.

19. The method of claim 17, wherein the appropriate locations for placing the one or more electrodes are identified further based on pre-stored information corresponding to the subject.

20. The method of claim 17, wherein the collected recorded signal parameters are determined as incorrect when the recorded signal parameters exceed a predefined threshold level.

21. The method of claim 17 further comprising providing one or more suggestions to a display when the recorded signals are determined as incorrect, the suggestions corresponding to a probable reason for incorrect recorded signals.

* * * * *